US009024047B2

(12) United States Patent
Kasat et al.

(10) Patent No.: US 9,024,047 B2
(45) Date of Patent: May 5, 2015

(54) METHODS FOR FURFURAL PRODUCTION FROM BRANCHED NON-FERMENTABLE SUGARS IN STILLAGE OR SYRUP

(75) Inventors: Rahul B Kasat, Wilmington, DE (US); Subramaniam Sabesan, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 14/009,645

(22) PCT Filed: Dec. 20, 2011

(86) PCT No.: PCT/US2011/066334
§ 371 (c)(1),
(2), (4) Date: Oct. 3, 2013

(87) PCT Pub. No.: WO2012/088208
PCT Pub. Date: Jun. 28, 2012

(65) Prior Publication Data
US 2014/0051873 A1  Feb. 20, 2014

Related U.S. Application Data

(60) Provisional application No. 61/425,288, filed on Dec. 21, 2010.

(51) Int. Cl.
C07D 307/50 (2006.01)
C07D 307/48 (2006.01)

(52) U.S. Cl.
CPC ............ *C07D 307/50* (2013.01); *C07D 307/48* (2013.01)

(58) Field of Classification Search
CPC ..................................... C07D 307/50
USPC .......................................... 549/489
See application file for complete search history.

(56) References Cited

U.S. PATENT DOCUMENTS

| 2,536,732 | A | 1/1951 | Dunlop |
| 2,559,607 | A | 7/1951 | Dunning |
| 2,750,394 | A | 6/1956 | Peniston |
| 4,154,744 | A | 5/1979 | Hamada |
| 4,366,322 | A | 12/1982 | Raymond |
| 4,503,023 | A | 3/1985 | Breck |
| 4,533,743 | A | 8/1985 | Medeiros |
| 6,441,202 | B1 | 8/2002 | Lightner |
| 6,743,928 | B1 | 6/2004 | Zeitsch |
| 7,572,925 | B2 | 8/2009 | Dumesic |
| 8,277,521 | B2 | 10/2012 | Gruier |
| 8,314,260 | B2 | 11/2012 | Gruter |
| 8,389,749 | B2 | 3/2013 | Dumesic |
| 8,399,688 | B2 | 3/2013 | Dumesic |
| 2003/0032819 | A1 | 2/2003 | Lightner |
| 2007/0298477 | A1 | 12/2007 | Kratochvil |
| 2008/0033187 | A1 | 2/2008 | Zhao |
| 2008/0033188 | A1 | 2/2008 | Dumesic |
| 2009/0124839 | A1 | 5/2009 | Dumesic |
| 2009/0131690 | A1 | 5/2009 | Gruter |
| 2009/0156841 | A1 | 6/2009 | Sanborn |
| 2009/0306415 | A1 | 12/2009 | Gruter |
| 2010/0048924 | A1 | 2/2010 | Kilambi |
| 2010/0058650 | A1 | 3/2010 | Gruter |
| 2010/0212218 | A1 | 8/2010 | Gruter |
| 2010/0218415 | A1 | 9/2010 | Gruter |
| 2010/0218416 | A1 | 9/2010 | Gruter |
| 2010/0299991 | A1 | 12/2010 | Gruter |
| 2010/0317879 | A1 | 12/2010 | Zhao |
| 2011/0071306 | A1 | 3/2011 | Robinson |
| 2011/0144359 | A1 | 6/2011 | Heide |
| 2012/0108829 | A1 | 5/2012 | De Jong |
| 2012/0111714 | A1 | 5/2012 | Court |
| 2012/0157697 | A1 | 6/2012 | Burket |
| 2013/0017579 | A1 | 1/2013 | Luterbacher |

FOREIGN PATENT DOCUMENTS

| CN | 100999677 A | 7/2007 |
| CN | 101367782 A | 2/2009 |
| CN | 101486695 A | 7/2009 |
| EP | 2033958 A1 | 3/2009 |
| GB | 799603 A | 8/1958 |
| GB | 838957 A | 6/1960 |
| JP | 02-108682 A | 4/1990 |
| JP | 12065468 A | 10/1998 |

(Continued)

OTHER PUBLICATIONS

E. I. Fulmer et al., The Production of Furfural From Xylose Solutions by Means of Hydrochloric Acid-Sodium Chloride Systems, Department of Chemistry, Iowa, Journal of Physical Chemistry, vol. 40 (1936), pp. 133-141.

C. Liu et al., The Enhancement of Xylose Monomer and Xylotriose Degradation by Inorganic Salts in Aqueous Solutions at 180oC, Carbohydrate Research, vol. 341 (2006), pp. 2550-2556.

G. Marcotullio et al., Chloride Ions Enhance Furfural Formation From D-Xylose in Dilute Aqueous Acidic Solutions, Green Chemistry (2010), The Royal Society of Chemistry, pp. 1-8.

F. Tao et al., Efficient Process for the Conversion of Xylose to Furfural With Acidic Ionic Liquid, Can. J. Chem., vol. 89 (2011), pp. 83-87.

Blatter et al., The Preparation of Pure Zeolite Nay and Its Conversion to High-Silican Faujasite, J. Chem Ed., vol. 67 (1990), pp. 519-521.

(Continued)

*Primary Examiner* — Taofiq A Solola

(57) ABSTRACT

Furfural is obtained selectively and in good purity from non-fermentable branched sugars found in soluble waste streams of lignocellulosic biomass. In a monophasic method, stillage or syrup is contacted with water and an acid catalyst under suitable reaction conditions to convert the branched non-fermentable branched sugars to furfural. Additionally, the stillage or syrup can be treated with a water-immiscible organic solvent to form a biphasic mixture comprising an aqueous phase and an organic phase. The furfural that is produced preferentially partitions into the organic phase, from which it may be recovered.

11 Claims, No Drawings

(56) References Cited

FOREIGN PATENT DOCUMENTS

| | | |
|---|---|---|
| JP | 2007196174 A | 8/2007 |
| WO | 2011063500 A1 | 6/2011 |

OTHER PUBLICATIONS

Hutchings et al., Developments in the Production of Methyl Tert-Butyl Ether, Catalysis Today, vol. 15 (1992) pp. 23-49.

Karinen et al., Biorefining: Heterogeneously Catalyzed Reactions of Carbohydrates for the Production of Furfural and Hydroxymethylfurfural, Chem Sus Chem, vol. 4 (2011) pp. 1002-1016.

Chen, Hydrophobic Properties of Zeolites, Journal of Physical Chemistry, vol. 80, No. 1 (1976) pp. 60-64.

Dwyer, Zeolite Structure, Composition and Catalysis, Chemistry and Industry, vol. 2 (1984) pp. 258-269.

Gairola et al., Hydrothermal Pentose to Furfural Conversion and Simultaneous Extraction With SC—CO2, Kinectics and Application to Biomass Hydrolysates, Bioresource Technology, vol. 123 (2012), pp. 592-598.

Kawamoto et al., Catalytic Pyrolysis of Cellulose in Sulfolane With Some Acidic Catalysts, J Wood Sci, vol. 53 (2007), pp. 127-133.

Suzuki et al., Dehydration of Xylose Over Sulfated Tin Oxide Catalyst: Influences of the Preparation Conditions on the Structural Properties and Catalytic Performance, Applied Catalysis A: General, vol. 408 (2011), pp. 117-124.

Starr et al., High Sulfidity Pulping in Aqueous Sulfolane, TAPPI Alkaline Pulping Conference Preprints (1975), pp. 195-198.

Clermont, Delignification of Aspen Wood With Aqueous Sulfolane Solutions, TAPPI, vol. 53, No. 12 (1970), pp. 2243-2245.

Chheda et al., Production of 5-Hydroxymethylfufual and furfural by dehydration of biomass-derived mono- and poly-saccharides, Green Chemistry, 2007, 342-350, 9, The Royal Society of Chemistry.

Mamman et al., Furfural: Hemicellulose/xylose-derived biochemical, Biofuels, Bioproducts & Biorefining, 2008, 438-453, Wiley Interscience.

Vazquez et al., Hydrolysis of Sorghum Straw using Phosphoric Acid: Evaluation of Furfural Production, Bioresource Technology, 2007, 3053-3060, 98, Elsevier.

Amiri et al., Production of furans from rice straw by single-phase and biphasic systems, Carbohydrate Research, 2010, 2133-2138, vol. 345.

Weingarten et al., Kinetics of furfural production by dehydration of xylose in a biphasic reactor with microwave heating, Green Chemistry, The Royal Society of Chemistry, 2010, 1423-1429, vol. 12.

Zhao et al., Metal Chlorides in Ionic Liquid Solvents Convert Sugars to 5-Hydroxymethylfurfural, Science, 2007, 1597-1600, vol. 316.

Dias et al., Dehydration of xylose into furfural over micro-mesoporous sulfonic acid catalysts, Journal of Catalysis, 2005, 414-423, vol. 229.

METHODS FOR FURFURAL PRODUCTION FROM BRANCHED NON-FERMENTABLE SUGARS IN STILLAGE OR SYRUP

This application claims priority under 35 U.S.C. §119(e) from, and claims the benefit of, U.S. Provisional Application No. 61/425,288, filed Dec. 21, 2010, which is by this reference incorporated in its entirety as a part hereof for all purposes.

FIELD OF THE INVENTION

Methods for the production of furfural from biomass stillage are provided. Specifically, methods for obtaining furfural selectively in good purity from the soluble waste stream of lignocellulosic biomass of biofuel industry under monophasic and biphasic conditions are provided.

BACKGROUND

Furfural and related compounds are useful precursors and starting materials for industrial chemicals for use as pharmaceuticals, herbicides, stabilizers, and polymers. Furfural is commonly made by dehydration of xylose or hemicellulose under acidic conditions. The current furfural manufacturing process utilizes biomass such as corn cob, switchgrass or wood waste as a raw material feed stock for obtaining xylose or hemicellulose, while very little value is obtained for the other major components such as cellulose and lignin except for energy production. With the evolution of ethanol industry, the availability such biomass material is expected to become limited. The objective of this invention is to render complete utilization of biomass, where the cellulose and a major portion of hemicellulose still can be directed toward biofuel production via enzymatic saccharification and fermentation followed by utilization of non-fermentable sugars in the waste stream for furfural production.

The production of ethanol from biomass, via enzymatic saccharification and fermentation of a major portion of hemicellulose and cellulose, results in the concurrent production of a waste stream known as "whole stillage" from distillation in the range of up to 20 liters of stillage per liter of ethanol. The carbohydrates in whole stillage comprise some non-fermentable branched pentose sugars in their oligomeric forms. Following solid/liquid separation of the whole stillage "thin stillage" is obtained. Thin stillage can be evaporated to produce the "syrup" which is burned to extract caloric values from it. Hereafter, whole stillage and thin stillage are referred to as "stillage".

An alternative means to using some of the non-fermentable sugars locked in the stillage or syrup, to minimize carbon waste and reduce the negative environmental impact resulting from burning of the syrup, is to develop methods to extract useful chemicals from it. For example, furan derivatives, such as hydroxymethylfuran (HMF) and furfural, which can serve as platforms for different chemicals and fuel productions, can be produced from agricultural waste material (Amiri, H. et al., Carbohydrate Research, 345(15), (2010) 2133-2138).

Conventionally, furfural can be produced from pentose sugars obtained from hydrolysis of the hemicellulose contained in biomass. Typically, hydrolysis of biomass is performed with aqueous acids at relatively high temperatures to obtain $C_5$ and $C_6$ sugars derived from xylan and glucan, respectively. Any furfural generated in this process, when left in the monophasic aqueous reaction mixture of sugars, can undergo degradation via condensation initiated by reactive sugar intermediates, resulting in lower yield of the desired furfural product. Furthermore, costly separation steps are then required to isolate the furfural from other intermediates, thus increasing complexity of the process.

U.S. Patent Application Publication No. 2008/0033188 relates to a process to make furan derivative compounds. The process comprises dehydrating a carbohydrate feedstock solution, optionally in the presence of an acid catalyst, in a reaction vessel containing a biphasic reaction medium comprising an aqueous reaction solution and a substantially immiscible organic extraction solution. The aqueous reaction solution, the organic extraction solution, or both the aqueous reaction solution and the organic extraction solution, contain at least one modifier to improve selectivity of the process to yield furan derivative compounds in general, and HMF in particular.

Current methods do not describe complete utilization of all the valuable carbohydrates in the biomass. In particular, methods for producing useful chemicals from non-fermentable branched sugars in stillage or syrup are therefore highly desirable.

SUMMARY

Described herein are methods for conversion of non-fermentable branched sugars in stillage or syrup, resistant to hydrolysis by glycosidase enzymes, to furfural. The disclosed method involves adding an acid catalyst to a mixture of water with stillage or syrup and heating the mixture at high temperatures. Alternatively, a biphasic reaction comprising one or more water-immiscible organic solvents can be used for conversion of non-fermentable branched sugars of stillage or syrup to furfural, which is preferentially partitioned into the organic phase.

In one embodiment, the method for furfural production comprises the steps of:
 a) providing stillage or syrup comprising non-fermentable branched sugars;
 b) contacting the stillage or syrup with water to form a mixture;
 c) acidifying the mixture formed in step (b) to pH 1 or less with an acid catalyst;
 d) heating the acidified mixture formed in step (c) at a temperature and for a time sufficient to convert the non-fermentable branched sugars to furfural; and
 e) optionally, recovering the furfural thereby produced.

In another embodiment, the method to produce furfural further comprises contacting the mixture acidified in step c) with at least one water-immiscible organic solvent comprising at least one aliphatic hydrocarbon, cycloalkane, aromatic hydrocarbon, polyether containing ester or ether end groups, plant-derived oil, or mixtures thereof under suitable reaction conditions to form a mixture comprising an aqueous phase and a furfural-containing organic phase.

DETAILED DESCRIPTION OF THE INVENTION

Definitions

The methods described herein are described with reference to the following terms.

As used herein, where the indefinite article "a" or "an" is used with respect to a statement or description of the presence of a step in a method of this invention, it is to be understood, unless the statement or description explicitly provides to the contrary, that the use of such indefinite article does not limit the presence of the step in the method to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "invention" or "present invention" as used herein is a non-limiting term and is not intended to refer to any single variation of the particular invention but encompasses all possible variations described in the specification and recited in the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" can mean within 10% of the reported numerical value, preferably within 5% of the reported numerical value.

As used herein, the term "water-immiscible" refers to a solvent or solvent mixture which is incapable of mixing with water or an aqueous solution to form one liquid phase.

As used herein, the term "monophasic" refers to a reaction medium that includes only one liquid phase. Some examples are water, aqueous solutions, and solutions containing aqueous and organic solvents that are miscible with each other. The term "monophasic" is also used to describe a method employing such a reaction medium, As used herein, the term "biphasic" refers to a reaction medium that includes two immiscible liquid phases, for example, an aqueous phase and a water-immiscible organic solvent phase. The term "biphasic" is also used to describe a method employing such a reaction medium, As used herein, the term "whole stillage", also known as distillery wastewater, distillery pot ale, distillery slops, distillery spent wash, dunder, mosto, or vinasse, refers to the components at the bottom of a distillation column produced during fermentation of biomass carbohydrates to ethanol. The whole stillage contains any solids and salts from a distillation feed stream. Whole stillage is therefore a type of fermentation broth depleted from the fermentation product(s). The whole stillage contains between 8-12 weight percent of total solids, is moderately acidic (pH~5) and has a high chemical oxygen demand value (COD~50,000 mg per liter).

As used herein, the term "thin stillage" refers to a liquid fraction resulting from solid/liquid separation of a whole stillage, fermentation broth, or product depleted fermentation broth. The thin stillage contains between 5 and 7 weight percent of total solids, is moderately acidic (pH~5.5).

As used herein, the term "stillage" refers to either whole stillage or thin stillage or both.

As used herein, the term "product depleted broth" or "depleted broth" refers to a fermentation broth after removal of a product stream.

As used herein, the term "syrup" means a concentrated product produced from the removal of water, generally by evaporation, from thin stillage. The syrup contains between 30 and 70 weight percent of total solids.

In one embodiment, a method to convert non-fermentable branched sugars left in the stillage or syrup following conversion of biomass to products such as ethanol is provided. As used herein, the term "nonfermentable branched sugars" refers to oligomeric pentose sugars that are left in the stillage or syrup following removal of the product at the end of the biomass fermentation. Typically, these are 1,4-linked β-xylopyranoside oligomers on to which other sugars are attached to generate branched structures. These branched structures are resistant to glycosidic enzymes and as a result are left unutilized in a typical biomass saccharification mixture.

The non-fermentable branched oligomeric sugars in the stillage or syrup possess the general formula shown below where R can be an L-arabinofuranosyl group or a hydrogen:

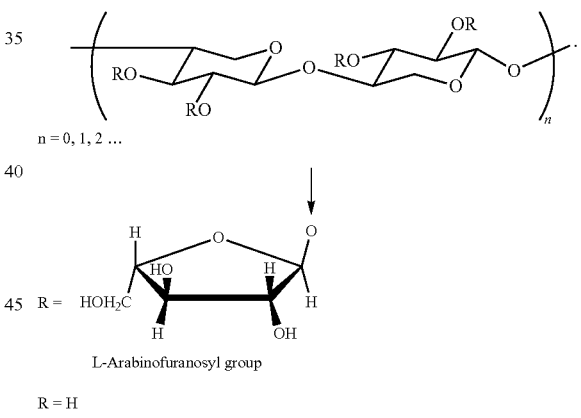

In these sugars, the hydroxyl groups of xylosyl units can be further glycosylated with one or two α-L-aranbinofuranosyl or substituted arabinofuranosyl units.

These sugars are resistant to hydrolysis by glycosidase enzymes and are often burned as waste. In the method described herein, the non-fermentable branched sugars in stillage or syrup are instead converted to furfural.

Following distillation and separation of the fermentation product from the fermentation broth, whole stillage which is depleted of the fermentation product is produced. The whole stillage can be separated into solid and liquid fractions. The liquid fraction is called "thin stillage" and is very low in suspended solids concentration and thus maintains a low viscosity during subsequent evaporation. The viscosity stays below about 100 centipoise throughout evaporation, allowing evaporation to at least about 40% solids or greater in the resulting syrup. Evaporation of the thin stillage produces a "syrup" that is at least about 30%, 40%, 45%, 50%, 55%, 60%, 65%, or 70% solids.

Depending on the type of fermentation, the level of solids in the thin stillage varies. For example, in a typical corn grain dry grind ethanol production process (a process wherein grain and not lignocellulosic biomass is used as a source of fermentable sugars), the thin stillage has a much higher suspended solids concentration, becomes viscous during evaporation, and can only be evaporated to a syrup of less than 40% solids. The total suspended solids in the thin stillage from the corn grain dry grind process are typically about 2%-3%. In the present method, the thin stillage from a lignocellulosic biomass hydrolysate broth or depleted broth has less than 1,000 ppm, or 0.1%, suspended solids.

In the method described herein, whole stillage can be heated in any system capable of maintaining temperature for the desired time. For example, heating can be performed in a heat jacketed vessel or in a heat exchanger with subsequent hold in a vessel or pipe loop.

One skilled in the art, with knowledge of the results in the examples provided herein, can determine a temperature and time within the given ranges that is appropriate for a specific overall process. For example, a 30 second treatment at 110° C. to 145° C. can readily be achieved using a residence time pipe loop, which allows a continuous process to be used, and no jacketed vessel is required making this particular set-up economically attractive. Alternatively, if a lower temperature is desired, such as 95° C. to 100° C., which is the temperature of whole stillage from an atmospheric distillation, then a time of about fifteen to 30 minutes would be used. As in this case, if the temperature of the whole stillage is at or above the desired temperature due to a previous process step, no further application of heat may be required; the temperature is maintained for the desired time by holding the whole stillage in an insulated vessel for the required period of time.

Stillage or syrup suitable for the current method can be obtained from treatment of biomass derived from a single source, or a mixture derived from more than one source; for example, biomass could comprise a mixture of corn cobs and corn stover, or a mixture of grass and leaves. Stillage or syrup from biomass sources such as bioenergy crops, agricultural residues, municipal solid waste, industrial solid waste, sludge from paper manufacture, yard waste, wood and forestry waste or a combination thereof can be used. Examples of biomass that can be used to provide the stillage or syrup include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof.

In one embodiment, the stillage or syrup is obtained from corn cobs, corn stover, switchgrass, wheat straw, sawdust, and sugar cane bagasse.

Solids from the whole stillage can be separated to allow for about 0.1% suspended solids in the whole stillage. Any separation method that produces thin stillage can be used. Various filtration devices can be used, such as a belt filter, belt press, screw press, drum filter, disc filter, Nutsche filter, filter press or filtering centrifuge to filter out the solids. Filtration can be aided, for example, by application of vacuum, pressure, or centrifugal force. In addition, a combination of separation processes can be used to achieve low suspended solids concentration, such as centrifugation followed by a small filter press to remove suspended solids that remain after centrifugation.

To improve efficiency of filtration, heat treatment, at a temperature that is between about 70° C. and about 150° C. for a time that is between about 30 seconds and 210 minutes, can be used. Longer times are used with lower temperatures in the range, and shorter times are used with higher temperatures in the range. Treating with heat can be carried out in any system capable of maintaining temperature for the desired time. For example, heating can be in a heat jacketed vessel or in a heat exchanger with subsequent hold in a vessel or pipe loop.

Following liquid/solid separation, a portion of the liquid fraction can be recycled for use directly as back set. As back set, the liquid could be added at any point in the process where fresh water is needed, such as in pretreatment, saccharification, or biocatalyst seed production. The remainder, or all, of the liquid fraction is further purified by evaporation producing water that can be recycled and a syrup. Because of the low suspended solids concentration in the liquid fraction (i.e., the thin stillage), evaporation can be used to produce a syrup with at least about 30% total solids, which is a combination of suspended and dissolved solids. Evaporation may be carried out at greater than atmospheric pressure, at atmospheric pressure, or with reduced pressure.

In the method described herein, stillage or syrup comprising non-fermentable branched sugars is contacted with water in the presence of an acid catalyst. Water may not be required when using either whole stillage or thin stillage. However, it is preferred to add water when using the syrup.

In one embodiment, an amount of water is used which is at least equivalent to that of the stillage on a weight basis. Typically, the use of more water provides a more dilute solution of pentosan sugars (from hydrolysis of the branched non-fermentable sugars contained in the stillage), which enables a higher overall selectivity of furfural to be realized. However, minimizing the amount of water used generally improves process economics by reducing process volumes and energy required for water recycling. In practical terms, the amount of water used relative to the stillage or syrup will depend on the moisture content of the stillage or syrup and on the desired yield of furfural, as well as the ability to provide sufficient mixing, or intimate contact, for the stillage or syrup and furfural production reactions to occur at a practical rate.

The acid catalyst comprises a mineral acid, a heteropolyacid, an organic acid, or a combination thereof. In one embodiment, the acid catalyst is a mineral acid comprising sulfuric acid, phosphoric acid, hydrochloric acid, or a combination of these. In one embodiment, the acid catalyst is a heteropolyacid comprising phosphotungstic acid, molybdophosphoric acid, or a combination of these. In one embodiment, the acid catalyst is an organic acid comprising oxalic acid, formic acid, acetic acid, an alkyl sulfonic acid, an aryl sulfonic acid, a halogenated acetic acid, a halogenated alkylsulfonic acid, a halogenated aryl sulfonic acid, or a combination of these. An example of a suitable alkyl sulfonic acid is methane sulfonic acid. An example of a suitable aryl sulfonic acid is toluenesulfonic acid. An example of a suitable halogenated acetic acid is trifluoroacetic acid. An example of a suitable halogenated alkylsulfonic acid is trifluoromethane sulfonic acid. An example of a suitable halogenated aryl sulfonic acid is fluorobenzenesulfonic acid.

The acid catalyst catalyzes hydrolysis of the xylooligomers contained in the stillage or syrup to monomeric sugars, and also the conversion of xylose and arabinose to furfural. The concentration of the acid catalyst in the aqueous solution is selected to provide acceptable rates of xylooligomer conversion to furfural (through the combination of hydrolysis and xylose/arabinose dehydration) while minimizing unwanted side reactions. In one embodiment, the acid catalyst can be combined with at least a portion of the water and contacted with the stillage or syrup feedstock as an aqueous solution. The acid catalyst can be obtained from commercial sources or prepared according to known methods.

When only one liquid phase is present, such as an aqueous solution or a solution containing aqueous and organic solvents that are miscible with each other, the method is referred to as "monophasic." In another embodiment, a "biphasic" method can be used, in which furfural that is produced in an aqueous phase then preferentially partitions into an organic solvent or solvent mixture. Organic solvents useful in the methods described herein are water-immiscible. A suitable organic solvent or solvent mixture should meet the criteria for an ideal solvent for two liquid phase production or recovery of furfural. Specifically, the organic solvent composition should (i) be substantially immiscible with water or the aqueous phase, (ii) have a high partition coefficient ($K_P$) for the extraction of furfural, and (iii) have a low tendency to form emulsions with water or the aqueous phase. In addition, for improved process operability and economics, the organic solvent should have a boiling point suitable for downstream separation of the solvent and the furfural. The boiling point can affect the cost and method of furfural recovery. For example, in the case where the furfural is recovered from the organic phase by distillation, the boiling point of the organic solvent should be sufficiently higher or lower than furfural as to enable facile distillation of the furfural from the solvent or distillation of the solvent from furfural.

Water-immiscible organic solvents useful in the methods described herein comprise at least one aliphatic hydrocarbon, cycloalkane, aromatic hydrocarbon, polyether having ester or ether end groups, plant-derived oil, or mixtures thereof. As used herein, the term "mixtures thereof" encompasses both mixtures within and mixtures between the solvent classes, for example mixtures within aliphatic hydrocarbons, and also mixtures between aliphatic hydrocarbons and aromatic hydrocarbons, for example.

The organic solvent can be one or more aliphatic hydrocarbons, for example an aliphatic hydrocarbon having from 5 to about 12 carbon atoms. The aliphatic hydrocarbon can be linear or branched. Optionally, the aliphatic hydrocarbon can be substituted, for example with at least one halogen atom. In one embodiment, the organic solvent is an aliphatic hydrocarbon comprising $CF_3CH_2CH_2CHF_2$, $CF_3CF_2CFHCFHCF_3$, $CF_3CF_2CHCl_2$, or mixtures thereof.

The organic solvent can be one or more cycloalkanes, for example a cycloalkane having from 6 to about 8 carbon atoms. The cycloalkane can be unsubstituted or substituted, for example with at least one halogen atom. In one embodiment, the organic solvent is a cycloalkane comprising cyclohexane, methylcyclohexane, or mixtures thereof.

The organic solvent can be one or more aromatic hydrocarbons, for example an aromatic hydrocarbon having from 6 to about 8 carbon atoms. The aromatic hydrocarbon can be substituted, for example with alkyl, halogenated alkyl, or halogen substituents. In one embodiment, the organic solvent is an aromatic hydrocarbon comprising benzene, toluene, a xylene, trifluorotoluene, or mixtures thereof.

The organic solvent can be a polyether of sufficient molecular weight to be immiscible in water and having ester or ether end groups of one to six carbon atoms. Polyethers having ester end groups can be obtained commercially or by reacting polyethers having hydroxyl end groups with carboxylic acids under appropriate reaction conditions, for example by reacting polyethylene glycol with acetic anhydride and pyridine, a reaction method well known in the art. The ester end groups can be linear or branched and can include, for example, acetate, propionate, or butyrate groups. Polyethers having ether end groups can be obtained commercially or by reacting polyethers having hydroxyl end groups with alcohols under appropriate reaction conditions, for example by reacting polyethylene glycol with benzyl iodide and sodium hydride, a methodology well known in the art (Theodora W. Greene, Peter. G. M. Wuts, *Protective Groups in Organic Synthesis*, Second Edition, John Wiley & Sons, INC, New York 1991). The ether end groups can be linear or branched and can include, for example, methoxy, ethoxy, propoxy, or butoxy groups. The polyether can include polyethylene glycol or polypropylene glycol, for example. In one embodiment, the organic solvent is a polyether comprising polyethylene glycol having ester or ether end groups, polypropylene glycol having ester or ether end groups, or mixtures thereof.

The organic solvent can be at least one plant-derived oil. In one embodiment, the plant-derived oil can comprise one or more free fatty acids. For example, the plant-derived oil can comprise lauric acid, myristic acid, palmitic acid, or a combination of these. In one embodiment, the plant-derived oil can comprise one or more triglycerides, wherein the triglycerides are derived from a fatty acid.

In one embodiment, the plant-derived oil can comprise triglycerides derived from a plant selected from the group consisting of corn, pine, rape seed, canola, sunflower, jathropa, seashore mallow, and combinations of two or more thereof. Oil from genetically modified plant varieties can also be used, for example genetically modified high stearic acid or high lauric acid canola varieties. In one embodiment, the plant-derived oil can be a vegetable oil selected from the group consisting of corn oil, coconut oil, palm kernel oil, palm oil, soybean oil, and cottonseed oil, or mixtures thereof.

Table 1 shows the fatty acid chain lengths of several triglyceride and fatty acid sources by weight percent. The fatty acid chain lengths in Table 1 are given using lipid nomenclature of the form C:D, where C is the number of carbon atoms in the fatty acid and D is the number of double bonds in the fatty acid. For example, C18:1 refers to an 18 carbon chain with 1 unsaturated bond, C18:2 refers to an 18 carbon chain with 2 unsaturated bonds, and C18:3 refers to an 18 carbon chain with 3 unsaturated bonds. In Table 1, $C_{18+}$ refers to fatty acids containing greater than 18 carbons. The values in Table 1 are representative of the triglyceride content of the indicated oils, which can vary from sample to sample.

TABLE 1

Fatty acid chain lengths of triglyceride and fatty acid sources (by weight percent).

|  | Coconut Oil | Palm Kernel Oil | Palm Oil | Soybean Oil |
| --- | --- | --- | --- | --- |
| C6:0 | 0.5 | | | |
| C8:0 | 7.5 | 3.5 | | |
| C10:0 | 5.8 | 3.4 | | |
| C12:0 | 45.6 | 46.2 | | |
| C14:0 | 18.4 | 17.0 | 1.0 | |
| C16:0 | 9.2 | 8.8 | 45.4 | 10.2 |
| C16:1 | | | | |
| C18:0 | 3.5 | 3.0 | 4.3 | 4.4 |
| C18:1 | 6.2 | 15.0 | 38.8 | 23.3 |
| C18:2 | 2.8 | 3.1 | 9.9 | 53.2 |
| C18:3 | | | | 6.5 |
| $C_{18+}$ Free Acids | 0.5 | | 0.6 | 2.4 |
| Total | 100.0 | 100.0 | 100.0 | 100.0 |

The water-immiscible organic solvent can be added either with the water or after addition of the water to the stillage or syrup. In one embodiment, the step of contacting the stillage or syrup with water in the presence of an acid catalyst is performed prior to the step of contacting the mixture with at least one water-immiscible organic solvent to form a mixture comprising an aqueous phase and a furfural-containing organic phase.

The relative amounts of the water (or aqueous acidic solution) and the organic solvent can vary within a suitable range. In one embodiment, the volume ratio of water to organic solvent used to form a mixture comprising an aqueous phase and a furfural-containing organic phase is from about 95:5 to about 5:95. In one embodiment, the volume ratio of water to organic solvent is from about 10:1 to about 1:10. In one embodiment, the volume ratio of water to organic solvent is from about 5:1 to about 1:5. In one embodiment, the volume ratio of water to organic solvent is from about 2:1 to about 1:2. In some embodiments, the volume ratio of water to organic solvent is between and optionally including any two of the following values: 95:5, 90:10, 80:20, 70:30, 60:40, 50:50, 40:60, 30:70, 20:80, 10:90, and 5:95, The optimal range reflects maximization of the extraction process, for example balancing a relatively high partition coefficient for furfural with an acceptable solvent cost or an acceptable boiling point. For the processes described herein for the production or recovery of furfural from a stillage or syrup, the temperature, contacting time, pentosan content of the biomass, furfural concentrations in the aqueous and organic phases, relative amounts of organic solvent and water (or aqueous acidic solution), specific solvent(s) used, presence of other organic solutes, and presence of aqueous solutes are related; thus these variables can be adjusted as necessary within appropriate limits to optimize the process as described herein.

In the biphasic methods described herein, the ratio of the stillage or syrup to the sum of the aqueous acidic solution and the organic solvent can be from about 1:1 to about 1:250 on a weight basis. In some embodiments, the weight ratio of the stillage or syrup to the sum of the aqueous acidic solution and the organic solvent is between and optionally including any two of the following values: 1:1, 1:5, 1:10, 1:15, 1:20, 1:30, 1:40, 1:50, 1:60, 1:70, 1:80, 1:90, 1:100, 1:120, 1:140, 1:160, 1:180, 1:200, 1:220, 1:240, and 1:250, When expressed as a percentage, the solids loading can be from about 50% to about 0.4%; in one embodiment, from about 25% to about 5%. Useful ranges of solids loading are dependent on the viscosity of the stillage or syrup in combination with the acid catalyst, water, and water-immiscible organic solvent, and can be affected by the type of biomass used and the particle size, for example. The stillage or syrup concentration can be maximized to the extent possible to minimize the volume of the contacting vessel and to make the process more economical. From a practical viewpoint, high ratios of the weight of the stillage or syrup to the weight of water +water-immiscible solvent can be limited by the ability to provide sufficient mixing, or intimate contact, for contacting to occur at a practical rate.

Suitable reaction temperatures and times are similar for biphasic and monophasic methods described herein. The monophasic or biphasic reaction medium is heated to a temperature and for a time sufficient to convert the branched non-fermentable sugars to furfural.

Suitable reaction conditions to form a mixture comprising an aqueous phase and a furfural-containing organic phase include a temperature of about 100° C. to about 220° C., for example from about 120° C. to about 160° C.

The contacting of the stillage or syrup with water and a water-immiscible organic solvent can be carried out for a period of time ranging from about 10 seconds to about 30 hours, for example from 5 minutes to about 15 hours. Typically, the contacting can be from 1 hour to about 5 hours.

The contacting of the stillage or syrup with water and a water-immiscible organic solvent can be performed at a relatively high temperature for a relatively short period of time, for example at about 140° C. to about 220° C. for about 180 minutes to about 10 minutes.

For contacting of the stillage or syrup with water and a water-immiscible organic solvent, the temperature, contacting time, acid, acid concentration, amount of water, ratio of water to organic solvent, the stillage or syrup concentration, and the stillage or syrup type are related; thus, these variables can be adjusted as necessary to produce a two-phase mixture comprising an aqueous phase and a furfural-containing organic phase at a sufficient rate and in a practical manner.

The contacting of the stillage or syrup with water and a water-immiscible organic solvent can be performed in any suitable vessel, such as a batch reactor a continuous reactor. The suitable vessel can be equipped with a means, such as impellers, for agitating the stillage or syrup/acid mixture. Reactor design is discussed in Lin, K.-H., and Van Ness, H. C. (in Perry, R. H. and Chilton, C. H. (eds.), *Chemical Engineer's Handbook*, $5^{th}$ Edition (1973) Chapter 4, McGraw-Hill, NY). The contacting step can be carried out as a batch process, or as a continuous process. In one embodiment, contacting the stillage or syrup with a water-immiscible organic solvent can be performed in the same vessel as the contacting with water and an acid catalyst. In one embodiment, contacting the stillage or syrup with water in the presence of an acid catalyst can be performed in one vessel, and the resultant mixture transferred to another vessel for contacting with a water-immiscible organic solvent.

Contacting the stillage or syrup with water and a water-immiscible organic solvent under suitable reaction conditions as described herein above provides a mixture comprising an aqueous phase and an organic phase. Furfural (FF) preferentially partitions into the organic phase, decreasing the concentration of furfural in the aqueous phase. Appropriate choices of organic solvent and contacting conditions enable compounds such as hydroxymethylfurfural (HMF) to partition preferentially into the aqueous phase, which provides furfural in good purity, relatively free of HMF, in the organic phase. In one embodiment, the organic phase can further comprise HMF, and the ratio of FF:HMF in the organic phase is at least 10:1 on a weight basis. In one embodiment, the ratio of FF:HMF in the organic phase is at least 12:1 on a weight basis The furfural-containing organic phase can be separated from the aqueous phase using methods known in the art, including but not limited to, siphoning, decantation, centrifugation, using a gravity settler, membrane-assisted phase splitting, and the like. Recovery of the furfural from the furfural-containing organic phase can be done using methods known in the art, including but not limited to, distillation, adsorption by resins, separation by molecular sieves, pervaporation, and the like. Specifically, distillation can be used to recover the furfural from the furfural-containing organic phase. The organic solvent can be recycled to contact additional stillage or syrup.

EXAMPLES

The methods described herein are illustrated in the following examples. From the above discussion and these examples, one skilled in the art can ascertain the essential characteristics of this invention, and without departing from the scope thereof, can make various changes and modifications of the invention to adapt it to various uses and conditions.

Carbohydrate Composition

The syrup was obtained from a process for fermentation of biomass to ethanol and its sugar content was determined according to the NREL method NREL/TP-510-42618 and is shown in the Table below.

| CONTENTS OF ORIGINAL SYRUP | | |
|---|---|---|
| | Concentration | |
| | mg/mL | mg/g |
| HMF | 0 | 0 |
| Furfural | 0 | 0 |
| Total Glucose | 47.66 | 40.56 |
| Total Galactose | 16.47 | 14.02 |
| Total Xylose | 57.75 | 49.15 |
| Total Arabinose | 36.35 | 30.94 |
| % Total solids | | 51.4 |
| Density of Syrup (g/mL) | | 1.175 |

The following abbreviations are used: "C" is Celsius, "mm" is millimeter, "μm" is micrometer, "μL" is microliter, "mL" is milliliter, "min" is minute(s), "g" is gram(s), "wt" is weight, "wt %" means weight percent, "Temp" is temperature, "g/mL" is gram per milliliter, "mg/mL" is milligram per milliliter; "mg/g" is milligram per gram, "rpm" means revolutions per minute, "mL/min" is milliliter per minute.

General Procedures

Making Furfural from Stillage or Syrup Under Monophasic and Biphasic Conditions

To an aqueous solution of stillage or syrup of known sugar composition (total hexose and total pentose as indicated above) and solid content (typically 40-55% total solids for syrup and 5-12% total solids for stillage) concentrated sulfuric acid or hydrochloric acid was added to lower the pH to 1.0.

Preparation of furfural from pH adjusted stillage or syrup was performed in batch mode in mono and/or biphasic conditions using either a Parr autoclave or a microwave reactor. Parr mini bench top autoclave reactor (model 4561, Parr Instrument Co., Moline, Ill.) with all internal wetted parts constructed from ZR705 was employed. External fittings were constructed with 316 stainless steel. Heat was supplied by an external electrical mantle. In a typical reaction, a Parr Reactor cup was charged with the stillage or syrup whose pH was adjusted with $H_2SO_4$.

For the biphasic reaction, enough toluene was added to obtain an 88.2 wt % toluene loading (relative to total reaction mass). After the reactor cup was charged with the reactants the reactor was assembled and a pressure check was performed. Stirring (300 rpm) and heating were initiated. The reactions were brought to 150° C. using a 15 min ramp-up period and then held at temperature for the desired reaction time (60 min). At the end of the reaction time the reactor was rapidly cooled using an ice bath. Once the temperature had returned to nearly ambient temperature, any excess pressure was released and the reactor was disassembled. The reaction mixture was transferred to a transparent container and the aqueous and organic layers were allowed to separate.

The microwave reactions were performed with Biotage Initiator™ Sixty Reactor (Biotage, Charlottesville, Va. 22911). For each reaction a 20 mL microwave tube was charged with pH adjusted stillage or syrup. For biphasic reaction, enough toluene was added to obtain an 80.0 wt % toluene loading (relative to total reaction mass). The vials were capped and then using the microwave reactor the reactions were stirred and heated (150° C., 90 min with 20 s pre-stirring). At the end of the reaction time vials were cooled within 5 min inside the reactor. Once the temperature had returned to nearly ambient temperature, the reaction mixtures were transferred to scintillation vials.

High Performance Liquid Chromatography (HPLC)

The aqueous layer from PARR reactor or microwave reactor was analyzed for furfural content by HPLC. The HPLC instrument (Waters Alliance Model, Milford, Mass.) was equipped with a Bio-Rad HPX-87H column (Bio-Rad Laboratories, Hercules, Calif.), appropriate guard columns and a refractive index detector. The flow rate was 0.6 mL/min. The Bio-Rad column was maintained at 50° C. Aqueous samples (typically 50 μL) was injected into the system and eluted with 0.01 N aqueous sulfuric acid. For the biphasic reactions, a sample of the organic layer was mixed with an equal amount of water to extract furfural. The furfural content of this water was determined by HPLC and this value was extrapolated to quantify the furfural content of the entire organic layer using the partition force of furfural in toluene and water predetermined earlier. These values were used to determine the furfural yield for each reaction.

Example 1

Formation of Furfural from Syrup in a Monophasic Aqueous Medium Using a Parr Reactor An aqueous solution of syrup (151.6 g, starting pH 5.0)) was adjusted to pH 1.0 by dropwise addition of concentrated sulfuric acid (10.9 g). A portion (135.2 g) was heated in the Parr reactor to 150° C. for 60 min. The reaction mixture was processed and analyzed as described above. The yield of furfural was 292 mg.

Example 2

Formation of Furfural from Syrup in Biphasic Aqueous and Toluene Medium Using a Parr Reactor A suspension of pH adjusted syrup (16.2 g) and toluene (121.0 g) was heated in the Parr reactor to 150° C. for 60 min. The reaction mixture was processed and analyzed as described above. The yield of furfural was 349 mg. No xylose was left in the suspension.

Example 3

Formation of Furfural from Stillage in Monophasic Aqueous Medium Using a Microwave Reactor An aqueous solution of syrup (20.7 g, starting pH 5.0)) was adjusted to pH 1.0 by dropwise addition of concentrated hydrochloric acid (2.2 g). A portion (12.0 g) was heated in the microwave reactor to 150° C. for 90 min. The reaction mixture was processed and analyzed as described above. The yield of furfural was 93.5 mg.

Example 4

Formation of Furfural from Syrup in Biphasic Aqueous and Toluene Medium Using a Microwave Reactor A suspension of pH adjusted syrup (2.4 g) and toluene (9.6 g) was heated in the reactor to 150° C. for 90 min. The reaction mixture was processed and analyzed as described above. The yield of furfural was 42.7 mg.

The invention claimed is:

1. A method for producing furfural comprising the steps of:
   a) providing stillage or syrup comprising non-fermentable branched sugars;
   b) contacting the stillage or syrup with water to form a mixture;
   c) acidifying the mixture of formed in step (b) to pH 1 or less with an acid catalyst;
   d) contacting the acidic mixture with at least one water-immiscible organic solvent:
   e) heating the mixture formed in step (c) at a temperature and for a time sufficient to convert the non-fermentable branched sugars to furfural;
   f) optionally, recovering the furfural thereby produced, wherein the at least one water-immiscible organic solvent is an aliphatic hydrocarbon, cycloalkane, aromatic hydrocarbon, polyether containing ester or ether end groups, or plant-derived oil.

2. The method of claim 1, wherein steps (b) and (c) are performed concurrently.

3. The method of claim 1 wherein the product furfural is recovered by either distillation or selective extraction with a solvent.

4. The method of claim 1, wherein the acid catalyst comprises a mineral acid, a heteropolyacid, an organic acid, or a combination thereof.

5. The method of claim 4, wherein the acid catalyst comprises sulfuric acid, phosphoric acid, hydrochloric acid, phosphotungstic acid, molybdophosphoric acid, oxalic acid, formic acid, acetic acid, an alkyl sulfonic acid, an aryl sulfonic acid, a halogenated acetic acid, a halogenated alkylsulfonic acid, a halogenated aryl sulfonic acid, or a combination thereof.

6. The method of claim 1, wherein the organic solvent is an aliphatic hydrocarbon comprising $CF_3CH_2CH_2CHF_2$, $CF_3CF_2CFHCFHCF_3$, $CF_3CF_2CHCl_2$, or mixtures thereof; a cycloalkane comprising cyclohexane, methylcyclohexane, or mixtures thereof; or an aromatic hydrocarbon comprising benzene, toluene, a xylene, trifluorotoluene, or mixtures thereof.

7. The method of claim 1, wherein the organic solvent is a polyether comprising polyethylene glycol having ester or ether end groups, polypropylene glycol having ester or ether end groups, or mixtures thereof.

8. The method of claim 1, wherein the organic solvent is a plant-derived oil selected from the group consisting of corn oil, coconut oil, palm kernel oil, palm oil, soybean oil, and cottonseed oil, or mixtures thereof.

9. The method of claim 1, wherein the volume ratio of water to organic solvent is from about 95:5 to about 5:95.

10. The method of claim 1, wherein the organic solvent comprises toluene, trifluorotoluene, or corn oil.

11. The method of claim 1 wherein the step of recovering furfural comprises separation of organic layer and evaporation of the organic solvent.

* * * * *